(12) United States Patent
Wang

(10) Patent No.: US 11,338,085 B2
(45) Date of Patent: May 24, 2022

(54) MANUALLY-RETRACTABLE INTRAVENOUS INFUSION NEEDLE ASSEMBLY

(71) Applicant: Zuyang Wang, Shanghai (CN)

(72) Inventor: Zuyang Wang, Shanghai (CN)

( * ) Notice: Subject to any disclaimer, the term of this patent is extended or adjusted under 35 U.S.C. 154(b) by 184 days.

(21) Appl. No.: 16/708,160

(22) Filed: Dec. 9, 2019

(65) Prior Publication Data

US 2020/0114070 A1    Apr. 16, 2020

Related U.S. Application Data

(63) Continuation of application No. PCT/CN2018/090524, filed on Jun. 8, 2018.

(51) Int. Cl.
 *A61M 5/158* (2006.01)

(52) U.S. Cl.
 CPC ..... *A61M 5/158* (2013.01); *A61M 2005/1583* (2013.01); *A61M 2005/1585* (2013.01); *A61M 2005/1586* (2013.01); *A61M 2005/1587* (2013.01)

(58) Field of Classification Search
 CPC .. A61M 5/158; A61M 5/1583; A61M 5/1585; A61M 5/1586; A61M 5/1587; A61M 25/0631; A61M 25/0637; A61M 2005/3247; A61M 5/3243; A61M 5/3271; A61M 25/0612; A61M 25/0618; A61M 25/0625
 See application file for complete search history.

(56) References Cited

U.S. PATENT DOCUMENTS

| 5,573,512 | A | 11/1996 | van den Haak |
| 2003/0163095 | A1 | 8/2003 | Nakashima |
| 2004/0236287 | A1* | 11/2004 | Swenson ............ A61M 25/0637 604/177 |
| 2017/0143897 | A1* | 5/2017 | Mao ...................... A61M 5/158 |

FOREIGN PATENT DOCUMENTS

| CN | 1184677 A | 6/1998 |
| CN | 1660454 A | 8/2005 |
| CN | 104288866 A | 1/2015 |
| CN | 206198391 U | 5/2017 |
| CN | 107281586 A | 10/2017 |
| JP | 2001259029 A | 9/2001 |

* cited by examiner

*Primary Examiner* — Emily L Schmidt
*Assistant Examiner* — Joshua Parker Reddington

(57) ABSTRACT

A manually-retractable intravenous infusion needle assembly, including a needle holder, a needle tube, a built-in slidable sheath and a protective casing, where the needle holder includes a tubular portion and a tailstock portion; a rear end of the needle tube is mounted inside the tubular portion; the built-in slidable sheath is through and elongated and has a C-shaped cross-section; the tubular portion is mounted inside the built-in slidable sheath and can slide back and forth; the protective casing is an elongated, through and hollow casing; the built-in slidable sheath is mounted inside the protective casing. A locking structure is provided between the needle holder and the protective casing.

15 Claims, 19 Drawing Sheets

MANUALLY-RETRACTABLE INTRAVENOUS INFUSION NEEDLE ASSEMBLY

CROSS-REFERENCE TO RELATED APPLICATIONS

This application is a continuation of International Patent Application No. PCT/CN2018/090524, filed on Jun. 8, 2018, which claims the benefit of priority from Chinese Patent Application No. 201710432400.3, filed on Jun. 9, 2017. The contents of the afore-mentioned applications, including any intervening amendments thereto, are incorporated herein by reference.

TECHNICAL FIELD

This application relates to medical appliances, and more specifically to a manually-retractable intravenous infusion needle assembly.

BACKGROUND

Currently, the disposable safety infusion needle products widely used worldwide are limited in variety, which is mainly because that the infusion needle is too small in size to simultaneously meet the technical requirements and ensure the simple operation when a safety device is additionally provided. The hose-type recap infusion needle manufactured by Becton Dickinson and Company (BD, US) has been considered to be an effectively-used safe product, in which the outer hose attached to the rear end of the infusion needle can be extended to cover the needle tip to ensure the safe use after the injection. Though this product has simple structure and is suitable for the actual application, it involves inconvenient operation and potential safety risks for patients and users during use. Other safety infusion needles, for example, needles of large size, in the prior art are greatly limited in their applications since they fail to meet the technical requirements of the infusion needle and to enable the convenient operation.

The primary technical points of the safety infusion needle are described as follows.

(1) The vertical distance between the needle tube and the bottom of the needle base should not exceed 1.5 mm, otherwise a large oblique angle will be formed between the needle tube and the base, which may easily cause the needle tip to stab the blood vessel.

(2) The infusion needle should have an appropriate size since it will be fixed on the back of a patient's hand for a long time, otherwise it may cause the inconvenient use, and discomfort to the patient.

In the use of a conventional infusion needle, the operator often pulls up and holds the handle to pull out the needle tube, which will cause the needle tube to rotate inside the blood vessel, raising a potential risk of the needle tip in damaging the blood vessel. This is one of the reasons why the patients often suffering from infusion are prone to phlebitis. In addition, after use, the uncovered needle tube may easily lead to the occurrence of stab and secondary injuries, resulting in cross-contamination.

In addition to the inconvenient operation, the hose-type safety infusion needle produced by Becton Dickinson Co., (US) also involves secondary injury, and potential damages to the patient's blood vessel when the needle is pulled out.

Other safety infusion needles generally have the defect of failing to simultaneously meet the technical and safety requirements and enable the miniaturization and convenient use. Though some products are well designed, they are not suitable for the mass production.

SUMMARY

Given the above defects in the prior art, the objects of this application are to: (1) enable the safety infusion; (2) achieve the miniaturization; and (3) simplify the production process. The safe infusion is mainly reflected in (1) minimizing the potential damage to the patient's vessel during the infusion; (2) minimizing the risks of stab injuries and cross-infections during the operation; and (3) reducing the occurrence of secondary injury and environmental pollution during the treatment of medical waste. The miniaturization is achieved mainly by modifying the structure to meet the technical requirements of the infusion and make the patients feel comfortable. Moreover, the user is not required to change the operation habit, ensuring more convenient and comfortable operation. The simplified process facilitates the industrial production, which can significantly lower the cost on the premise of ensuring the quality and safety of the product.

In order to achieve the above-mentioned objects, this application provides a manually-retractable intravenous infusion needle assembly in a first aspect, comprising:

a needle holder;
a needle tube;
a built-in slidable sheath; and
a protective casing;
wherein:
the needle holder comprises a tubular portion and a tailstock portion; the tubular portion and the tailstock portion are arranged in a front-and-rear manner and are connected to each other; the tubular portion is configured for the arrangement of the needle tube; the tailstock portion is configured to connect a delivery tube;
the built-in slidable sheath is through and elongated and has a C-shaped cross-section;
the protective casing is a long, through and hollow casing;
a rear end of the needle tube is mounted inside the tubular portion; the tubular portion is mounted in the built-in slidable sheath and is capable of sliding back and forth; the tailstock portion is provided outside a rear end of the built-in slidable sheath; the built-in slidable sheath is mounted in the protective casing and is capable of sliding back and forth; the needle holder is capable of being locked to the protective casing;

a first locking structure is provided between the needle holder and the built-in slidable sheath to lock the needle holder; a second locking structure is provided between the built-in slidable sheath and the protective casing to lock the built-in slidable sheath; and a third locking structure is provided between the needle holder and the protective casing to lock the needle holder;

when the third locking structure is unlocked, the needle holder is pulled backward to allow the tubular portion to move to a locking position of the first locking structure such that the tubular portion is locked to the built-in slidable sheath; when the needle holder is continuously pulled backward, the built-in slidable sheath is driven to move to a locking position of the second locking structure to be locked to the protective casing, and in this case, the needle tube is completely covered by the protective casing and a tip of the needle tube does not exceed the protective casing.

In an embodiment, the first locking structure comprises a first positioning member and a first locking member; wherein the first positioning member is provided on an outer wall of the tubular portion and the first locking member is provided on an inner wall of the built-in slidable sheath; when the tubular portion is moved to the locking position of the first locking member, the first positioning member is locked by the first locking member such that the tubular portion fails to slip off from the built-in slidable sheath.

In an embodiment, the first positioning member comprises a sliding block; the sliding block is provided on an outer peripheral surface of a front end of tubular portion; the first locking member comprises a slotted hole and a first elastic arm; wherein the slotted hole is axially provided along the built-in slidable sheath; the first elastic arm is provided at a rear section of the slotted hole; the sliding block is limited to slide within the slotted hole; when the sliding block is moved to a rear end of the slotted hole, the first elastic arm is driven by the sliding block to generate elastic deformation to allow the sliding block to pass through; and when the sliding block arrives at the rear end of the slotted hole, the first elastic arm recovers to a normal state such that the sliding block is locked and fails to slide reversely.

In an embodiment, the positioning member further comprises two side sliding blocks; wherein the two side sliding blocks are respectively provided at two sides of the sliding block;

the first locking member further comprises two first chutes; wherein the two first chutes are axially provided at inner walls of two sides of the built-in slidable sheath along the built-in slidable sheath, respectively; the two side sliding blocks are respectively limited to slide within the two first chutes such that the tubular portion fails to radially slip off from the built-in slidable sheath.

In an embodiment, the second locking structure comprises a second positioning member and a second locking member; wherein the second positioning member is provided on the built-in slidable sheath and the second locking member is provided on an inner wall of the protective casing; when the built-in slidable sheath is moved to the locking position of the second locking member, the second positioning member is locked by the second locking member such that the built-in slidable sheath fails to slip off from the protective casing.

In an embodiment, the second positioning member comprises two bumps, wherein the two bumps are respectively provided on two axial sections of the built-in slidable sheath;

the second locking member comprises two second chutes and two second elastic arms; wherein the two second chutes are axially and symmetrically provided along the protective casing; the two second elastic arms are respectively provided at rear sections of the two second chutes;

the two bumps are respectively limited to slide within the two second chutes; when the two bumps are moved respectively along the two second chutes to rear ends of the two second chutes, the two second elastic arms are respectively driven by the two bumps to generate elastic deformation to allow the two bumps to pass through; and when the two bumps respectively arrive at the rear ends of the two second chutes, the two second elastic arms recover to a normal state such that the two bumps are locked and fails to slide reversely.

In an embodiment, the third locking structure comprises a third locking member and a third positioning member, wherein the third locking member is provided on the tailstock portion and the third positioning member is provided on an outer wall of the protective casing; when the third locking member is locked on the third positioning member, the tailstock portion is locked on the protective casing, a front end of the built-in slidable sheath is limited by an inner wall of the protective casing, and a rear end of the built-in slidable sheath is limited by the tailstock portion; when the third locking member is unlocked from the third positioning member, the needle holder is capable of being pulled backward.

In an embodiment, the tailstock portion comprises a tailstock body and an assembling member; wherein the tailstock body is connected to the tubular portion; a side surface of the tailstock body is connected to the assembling member; the assembling member is parallel to a central axis of the tubular portion and clings to the outer wall of the protective casing; the assembling member is capable of being pulled to move from a side surface;

the third locking member is provided on the assembling member; the third locking member comprises a recess and the third positioning member comprises a projection; and when the assembling member is pulled to move from the side surface, the recess is unlocked from the projection.

In an embodiment, the intravenous infusion needle assembly further comprises a wing; wherein the wing is sleeved on the assembling member; and when the wing is pulled from a side, the assembling member is pulled synchronously.

In an embodiment, the third locking structure comprises a third positioning member and a third locking member; wherein the third positioning member is provided on the tubular portion and the third locking member is provided on a front end of an inner wall of the protective casing;

when the third positioning member is locked by the third locking member, the tubular portion is locked inside the protective casing, a front end of the built-in slidable sheath is limited by an inner wall of the protective casing, and a rear end of the built-in slidable sheath is limited by the tailstock portion; when the third positioning member is unlocked from the third locking member, the tubular portion is capable of being pulled out from the built-in slidable sheath.

In an embodiment, the third positioning member comprises two side sliding blocks, wherein the two side sliding blocks are symmetrically provided at a front end of an outer wall of the tubular portion;

the third locking member comprises two elastically-deformable bevel bumps; the bevel bumps are symmetrically provided at a front end of an inner wall of the protective casing;

when the two side sliding blocks are respectively locked by the two bevel bumps, the tubular portion is locked inside the protective casing and the built-in slidable sheath is simultaneously limited by the tailstock portion; and when the tubular portion is pulled backward, the two side sliding blocks respectively drive the two bevel bumps to generate elastic deformation such that the two side sliding blocks respectively slide through the two bevel bumps and the needle holder is pulled backward out of the protective casing.

In an embodiment, the intravenous infusion needle assembly comprises a wing, wherein the wing is sleeved on the tailstock portion; the wing is a single wing or a double wing; two wings of the double wing are symmetrically provided and are overlapped after folded; and when the wing is held to be pulled backward, the needle holder is synchronously pulled.

In an embodiment, the third locking structure comprises a third positioning member and a third locking member, wherein the third positioning member is provided on the tailstock portion and the third locking member is provided at a rear end of the protective casing;

when the third positioning member is locked by the third locking member, the tailstock portion is locked at the rear end of the protective casing, a front end of the built-in slidable sheath is limited by an inner wall of the protective casing and a rear end of the built-in slidable sheath is limited by the tailstock portion; and when the third positioning member is unlocked from the third locking member, the tailstock portion is capable of being pulled backward to move.

In an embodiment, the tailstock portion comprises a tailstock body and two pressing members; wherein the tailstock body is connected to the tubular portion; the two pressing members are respectively connected to two sides of the tailstock body; the two pressing members are both parallel to a central axis of the tubular portion; the two pressing members are capable of being oppositely pressed;

the third positioning member comprises two hooks, wherein the two hooks are respectively provided at front ends of the two pressing members;

the third locking member comprises two slots, wherein the two slots are respectively provided at two sides of the rear end of the protective casing; and when the two pressing members are held to be oppositely pressed, the two hooks are respectively unlocked from the two slots.

In an embodiment, the intravenous infusion needle assembly comprises a wing; wherein the wing is sleeved on the protective casing; the wing is a single wing or a double wing; two wings of the double wing are symmetrically provided and are overlapped after folded.

In an embodiment, the protective casing consists of an upper casing and a lower casing, wherein the upper casing is buckled with the lower casing; the built-in slidable sheath is mounted inside the upper casing; and two axial sections of the built-in slidable sheath fit an inner wall of the lower casing.

In an embodiment, a maximum vertical distance between the needle tube and an outer wall of the lower casing is equal to or less than 1.5 mm to avoid a large bevel angel to be formed between the needle tube and a base of the needle tube, preventing the blood vessel from being stabbed by the needle.

This application employs a specially-designed needle holder, a protective casing matching with the needle holder and a built-in slidable sheath provided between the needle holder and the protective casing to form the main structure of a safety infusion needle. At the beginning of the infusion, the venipuncture is exactly the same as that using a conventional puncture needle. After the infusion, the protective casing is pressed by one hand, and the assembling member of the need holder or the tailstock portion is held by the other hand to allow the assembling member of the need holder or the tailstock portion to be unlocked and disengaged. Then the needle tube is pulled out from the patient according to a conventional method. After the needle holder is pulled out from the built-in slidable sheath to a limit position and the built-in slidable sheath is pulled out from the protective casing to a limit position, the needle tube is completely pulled back into the protective casing such that the needle holder is locked and fails to move back and forth, ensuring the safe operation.

Compared to the prior art, this application has the following beneficial effects.

1. Free of Stab Injury and Cross-Infection (1) This application is able to minimize the potential damage to the patient's vessel during the infusion.

(2) This application is able to minimize the risks of stab injuries and cross-infections during the operation.

(3) This application is able to reduce the occurrence of secondary injury and environmental pollution during the treatment of medical waste.

2. Miniaturization (1) This application employs a combined structure of needle holder, built-in slidable sheath and protective sheath, where the needle holder can be locked to the protective casing through the side-surface locking, front-end locking or rear-end locking. In this application, the miniaturization is enabled by modifying the structure, meeting the technical requirements of the infusion and making the patients feel comfortable.

(2) The user does not need to change the operation habit, ensuring more convenient and comfortable operation.

3. Simplified Production Process (1) This application has a simple and precise design and a simplified production process, facilitating the industrial production.

(2) This application involves low cost on the premise of ensuring the quality and safety of the product.

Figure 1:
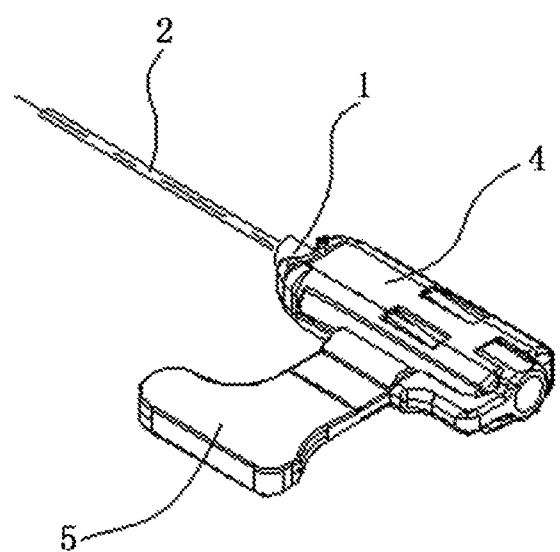
FIG. 1 schematically shows a manually-retractable intravenous infusion needle assembly according to Example 1 of the invention.

In the drawings, 1—needle holder; 11—tubular portion; 12—tailstock portion; 121—tailstock body; 122—assembling member; 1221—limiting portion; 1222—rod portion; 123—recess; 124—pressing member; 125—hook; 13—sliding block; 14—side sliding block; 2—needle tube; 21—needle tip; 3—built-in slidable sheath; 31—slotted hole; 311—rear-end through hole; 312—fishhook-like through hole; 32—first elastic arm; 33—first chute; 34—bump; 35—axial section; 4—protective casing; 41—upper casing; 42—lower casing; 421—second elastic arm; 422—projection; 423—bevel bump; 424—slot; 425—second chute; 5—wing; 51—shaft sleeve; 52—wing-like blade; 6—sleeve; 91—first locking structure; 911—first positioning member; 912—first locking member; 92—second locking structure; 922—second locking member; and 93—third locking structure.

DETAILED DESCRIPTION OF EMBODIMENTS

Described below are preferred embodiments of the invention, which are intended to more clearly illustrate the invention, so that those skilled in the art can fully understand the technical solutions of the invention. It should be understood that these embodiments and drawings are merely illustrative of the invention and are not intended to limit the invention. In the drawings, the members sharing the same structures are marked with the same numerical sign, and the components having similar functions or structures are marked with similar numerical signs.

Example 1

Figure 2:
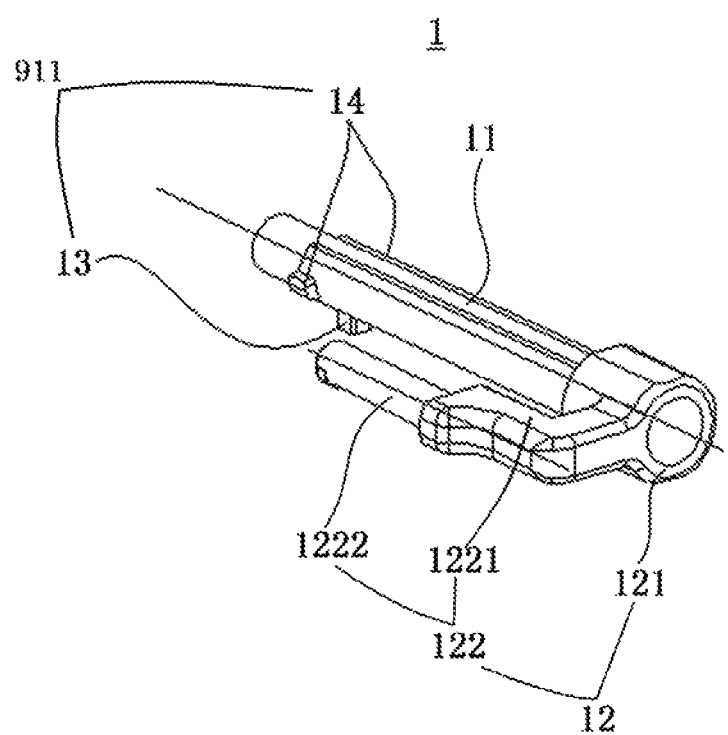
FIG. 2 schematically shows a needle holder of the manually-retractable intravenous infusion needle assembly according to Example 1 of the invention.

Referring to FIGS. 1-2, the invention provides a manually-retractable intravenous infusion needle assembly, including: a needle holder 1, a needle tube 2, a built-in slidable sheath 3 and a protective casing 4, where the needle holder 1 includes a tubular portion 11 and a tailstock portion 12; the tubular portion 11 has a hollow and cylindrical, and is configured for the arrangement of the needle tube 2; the tailstock portion 12 is larger than the tubular portion in diameter, and is configured to connect a delivery tube; a front end of the needle tube extends forward and a rear end of the needle tube is mounted inside the tubular portion 11; the tubular portion 11 is detachably mounted in the built-in slidable sheath 3 and can slide back and forth; the tailstock portion 12 is always located outside a rear end of the built-in slidable sheath 3; the protective casing 4 is a long, through and hollow casing; the built-in slidable sheath 3 is mounted in the protective casing 4 and can slide back and forth; the needle holder 1 can be locked to the protective casing 4. A first locking structure 91 is provided between the tubular portion 11 and the built-in slidable sheath 3 to lock the tubular portion 11; a second locking structure 92 is provided between the built-in slidable sheath 3 and the protective casing 4 to lock the built-in slidable sheath 3; and a third locking structure 93 is provided between the needle holder 1 and the protective casing 4 to lock the needle holder 1. When the third locking structure 93 is unlocked, the needle holder 1 is pulled backward to allow the tubular portion 11 to move to a locking position of the first locking structure 91 such that the tubular portion 11 is locked to the built-in slidable sheath 3; when the needle holder 1 is continuously pulled backward, the built-in slidable sheath 3 is driven to move to a locking position of the second locking structure 92 to be locked to the protective casing 4, and in this case, the needle tube 2 is completely covered by the protective casing 4 and a needle tip 21 does not exceed the protective casing 4.

Figure 3:
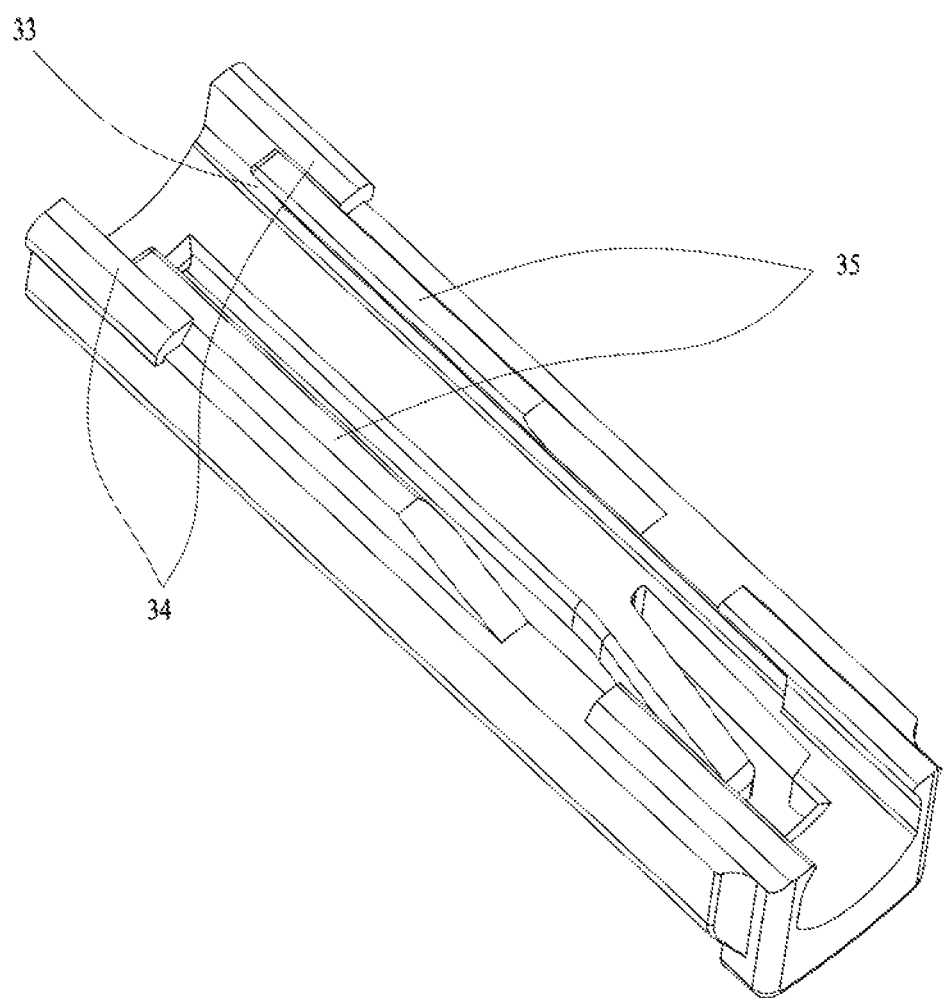
FIG. 3 schematically shows a built-in slidable sheath of the manually-retractable intravenous infusion needle assembly according to Example 1 of the invention.
Figure 4:
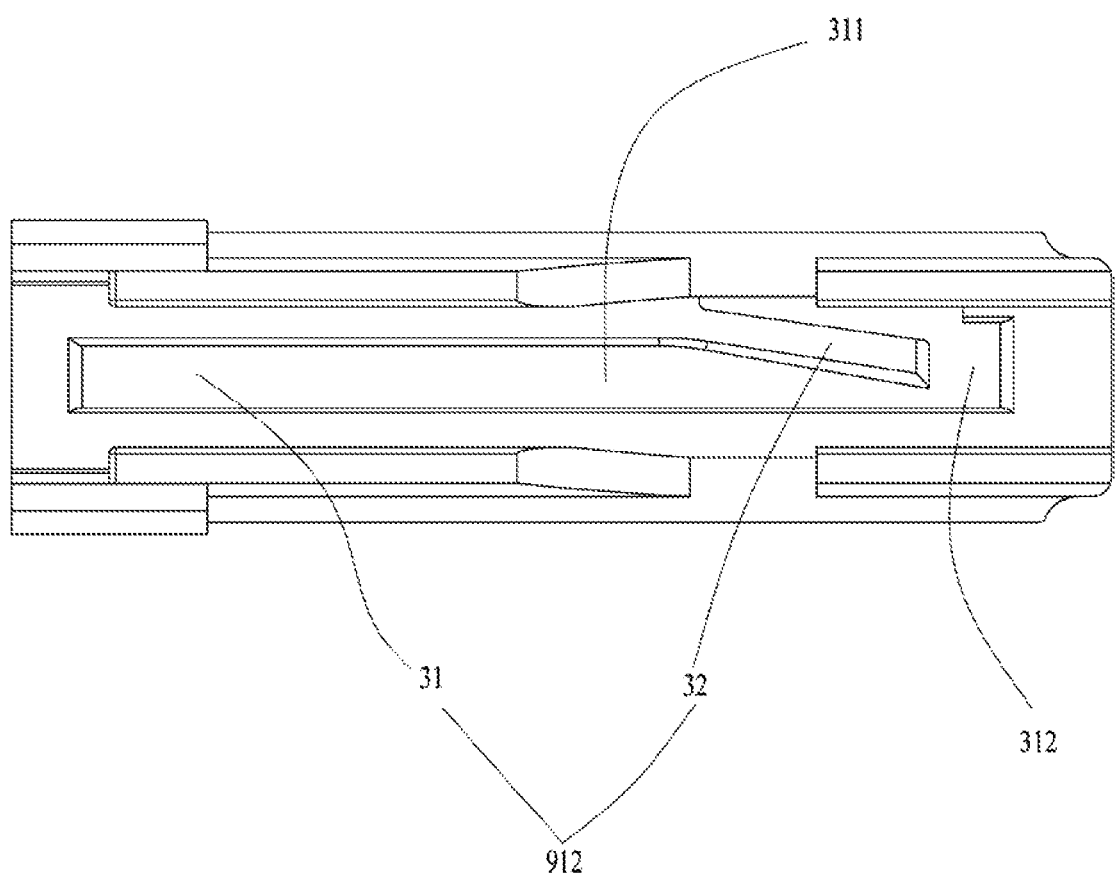
FIG. 4 is a bottom view of the built-in slidable sheath of the manually-retractable intravenous infusion needle assembly according to Example 1 of the invention.
Figure 5:
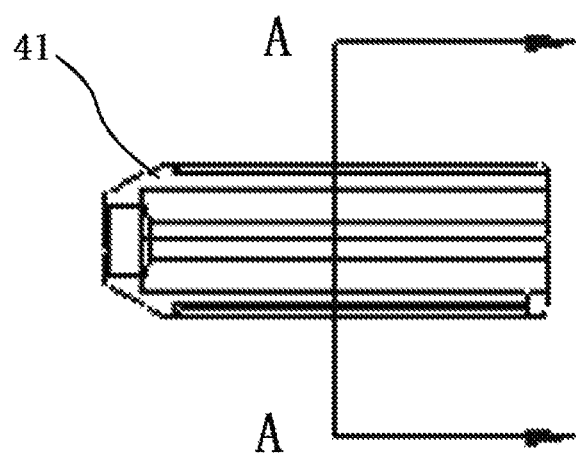
FIG. 5 schematically shows an upper protective casing of the manually-retractable intravenous infusion needle assembly according to Example 1 of the invention.
Figure 6:
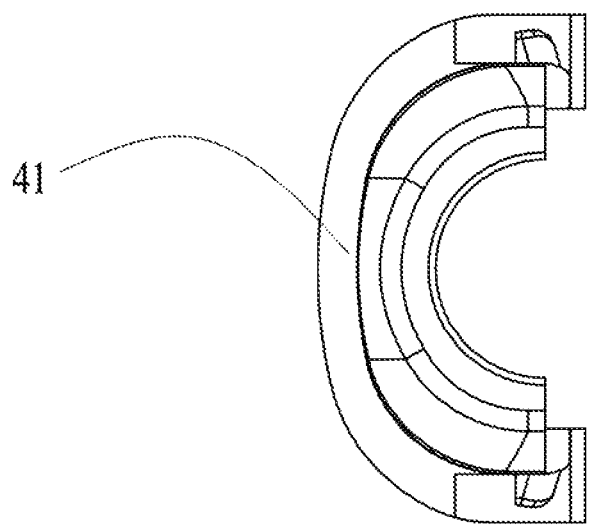
FIG. 6 is a sectional view of the upper protective casing of the manually-retractable intravenous infusion needle assembly according to Example 1 of the invention, taken along an A-A line of FIG. 5.
Figure 19:
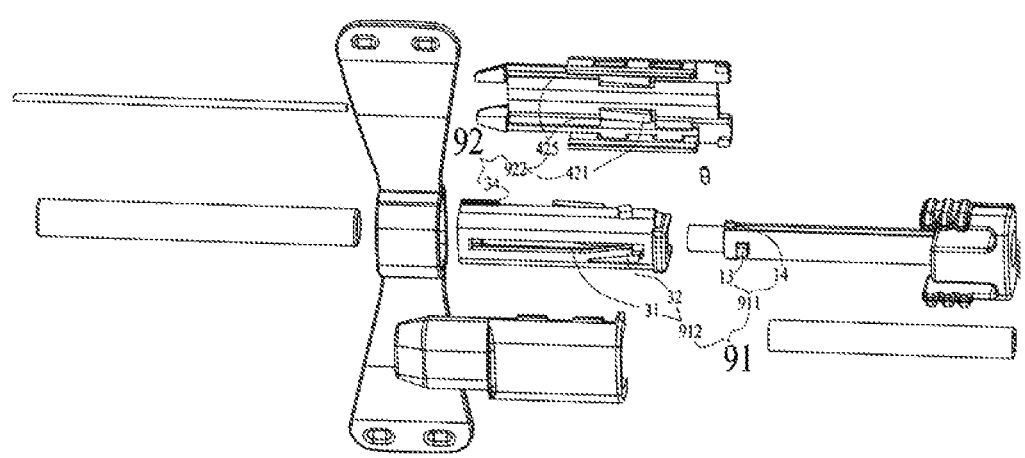
FIG. 19 is an explosive view schematically showing the manually-retractable intravenous infusion needle assembly of the invention.

As shown in FIG. 19, the first locking structure 91 includes a first positioning member 911 and a first locking member 912. As shown in FIG. 2, the first positioning member 911 is provided at a front end of an outer wall of the tubular portion 11 and includes a sliding block 13. The sliding block 13 is provided at the outer peripheral surface of the front end of the tubular portion 11. As shown in FIGS. 3-4, the built-in slidable sheath 3 having a C-shaped cross-section is through and elongated and an inner wall of the built-in slidable sheath 3 is provided with the first locking member 912. The first locking member 912 includes a slotted hole 31 and a first elastic arm 32, where the slotted hole 31 is axially provided along the built-in slidable sheath 3 and is located on a central line of the built-in slidable sheath 3 along a width direction; and the first elastic arm 32 is provided at a rear section of the slotted hole 31. Specifically, a rear-end through hole 311 with a gradually narrowing width is provided at a rear end of the slotted hole 31, and the rear-end through hole 311 is bent and extends toward a front end of the slotted hole 31 to form a fishhook-like through hole 312, providing the first elastic arm 32 in the rear-end through hole 311. The sliding block 13 is limited to slide within the slotted hole 31, and when the sliding block 13 is moved to the rear end of the slotted hole 31, the first elastic arm 32 is driven by the sliding block 13 to generate elastic deformation to allow the sliding block 13 to pass through; and when the sliding block 13 arrives at the rear end of the slotted hole 31, the first elastic arm 32 recovers to a normal state such that the sliding block 13 is locked in an axial direction of the built-in slidable sheath 3 and fails to slide reversely. After the tubular portion 11 is locked with the built-in slidable sheath 3, a rear end of the built-in slidable sheath 3 will be driven to slide out of the protective casing 4 in the case of continuously pulling the tailstock portion 12 backward.

As shown in FIG. 2, the first positioning member 911 further includes two side sliding blocks 14, which are symmetrically provided on two sides of the sliding block 13. As shown in FIGS. 3-4, the first locking member 912 further includes two first chutes 33, which are axially provided along the built-in slidable sheath 3 and are symmetrically provided on inner walls at two sides of the built-in slidable sheath 3. The two side sliding blocks 14 are respectively limited to slide within the two first chutes 33. In the case that the tubular portion 11 is mounted in the built-in slidable sheath 3, the movement of the tubular portion 11 along a radial direction will be limited such that the tubular portion 11 fails to slip out of the built-in slidable sheath 3 in the radial direction, enabling more stable assembly between the tubular portion 11 and the built-in slidable sheath 3.

Figure 7A:
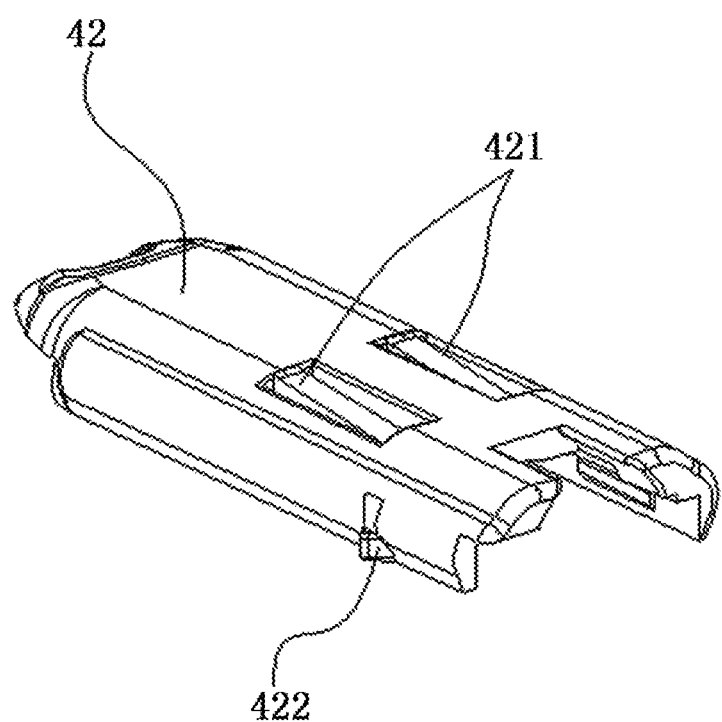
FIG. 7a schematically shows a lower protective casing of the manually-retractable intravenous infusion needle assembly according to Example 1 of the invention.
Figure 7B:
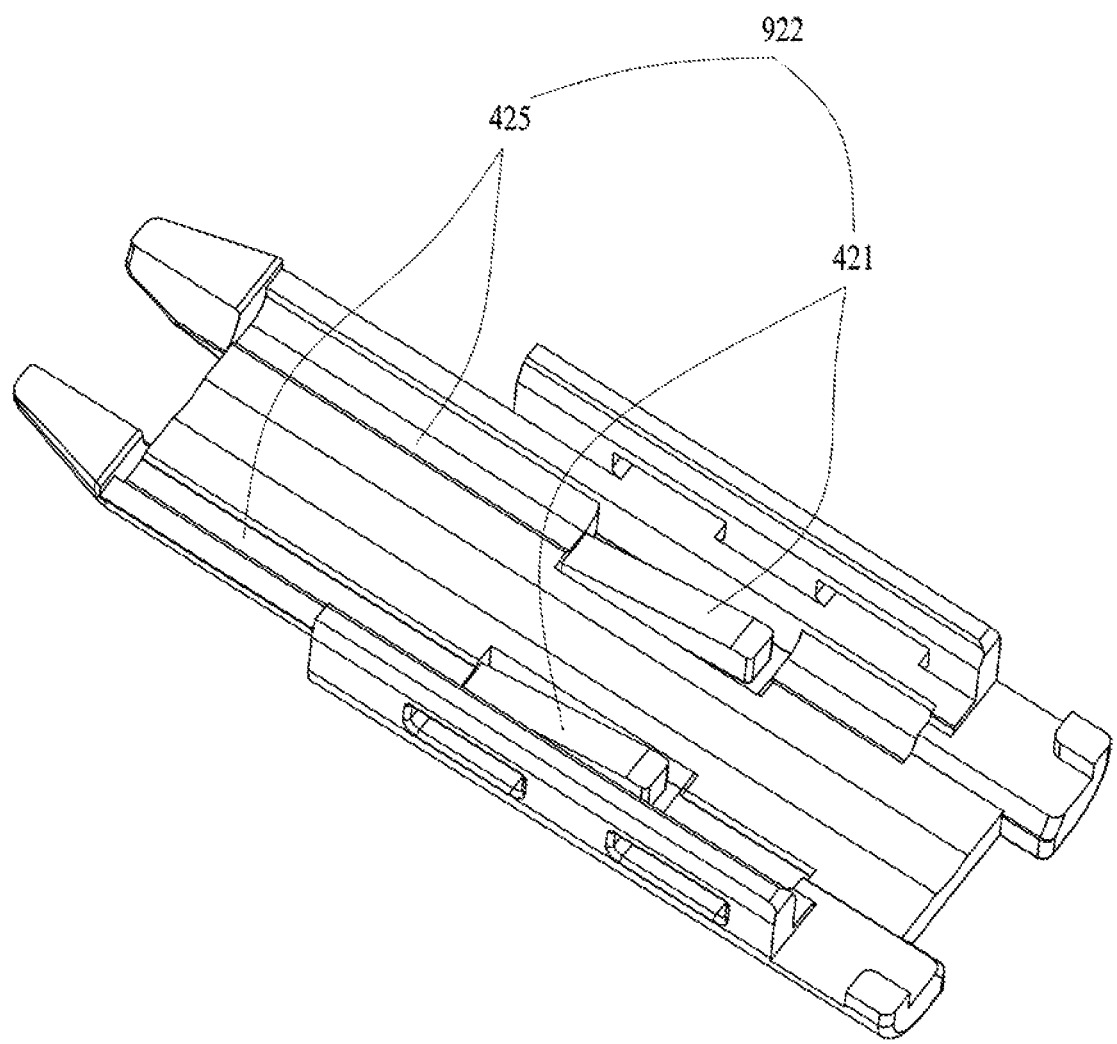
FIG. 7b schematically shows an inner structure of the lower protective casing of the manually-retractable intravenous infusion needle assembly according to Example 1 of the invention.
Figure 10:
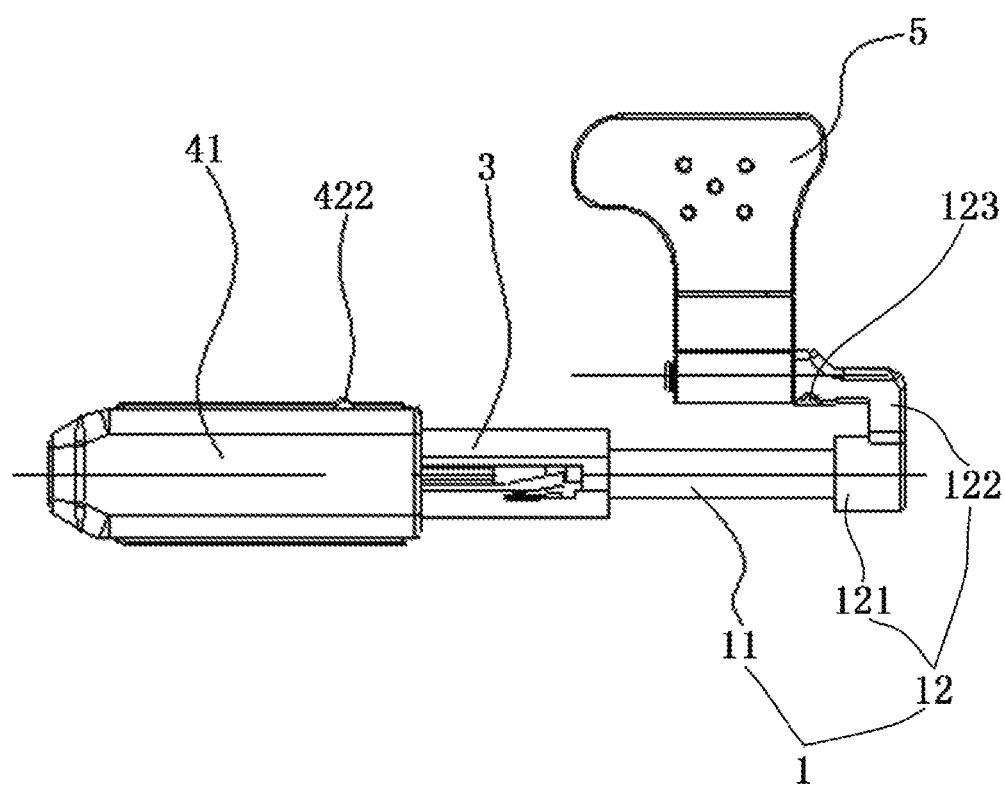
FIG. 10 schematically shows the manually-retractable intravenous infusion needle assembly according to Example 1 of the invention in an open state after use.

As shown in FIG. 19, the second locking structure 92 includes a second positioning member and a second locking member 922. As shown in FIG. 3, the second positioning member is provided on the built-in slidable sheath 3, and includes two bumps 34, where the two bumps 34 are respectively provided on two axial sections 35 of the built-in slidable sheath 3. As shown in FIGS. 1, 5, 7a and 7b, the protective casing 4 consists of an upper casing 41 and a lower casing 42, where the upper casing 41 is buckled with the lower casing 42. As shown in FIG. 7b, the cross sections of the upper casing 41 and the lower casing 42 are approximately U-shaped. The second locking member 922 is provided on an inner wall of the lower casing 42, and includes two second chutes 425 and two second elastic arms 421. The two second chutes 425 are symmetrically provided on the inside of the lower casing 42 along the axial direction of the lower casing 42. The two second elastic arms 421 are respectively provided at rear sections of the two second chutes 425. Referring to FIG. 10, the built-in slidable sheath 3 is mounted inside the upper casing 41, and two axial sections 35 of the built-in slidable sheath 3 fit the inner wall of the lower casing 42. The two bumps 34 are respectively limited to slide within the two second chutes 425. When the two bumps 34 are moved respectively along the two second chutes 425 to rear ends of the two second chutes 425, the two second elastic arms 421 are respectively driven by the two bumps 34 to generate elastic deformation to allow the two bumps 34 to pass through; and when the two bumps respectively arrive at the rear ends of the two second chutes 425, the two second elastic arms 421 recover to a normal state such that the two bumps are locked and fails to slide reversely.

Figure 9:
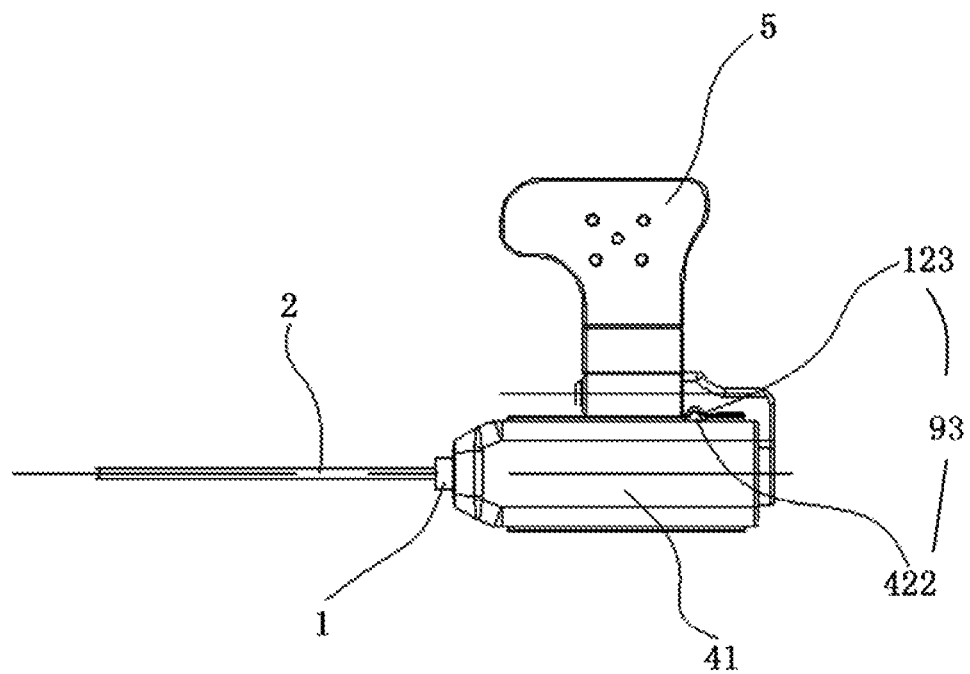
FIG. 9 schematically shows the manually-retractable intravenous infusion needle assembly according to Example 1 of the invention in a closed state before use.

In the third locking structure 93 of this embodiment, the needle holder 1 is locked with the protective casing 4 in a side locking manner. The third locking structure 93 includes a third positioning member and a third locking member 932. As shown in FIG. 7a, the third positioning member is provided on an outer wall of the lower casing 42, and is a triangular projection 422. As shown in FIGS. 2, 9 and 10, the third locking member 932 is provided on the tailstock portion 12. The tailstock portion 12 includes a tailstock body 121 and an assembling member 122, where the tailstock body 121 is connected to the tubular portion 11; a side of the tailstock body 121 is connected to the assembling member 122; the assembling member 122 is parallel to a center axis of the tubular portion 11 and clings to an outer wall of the protective casing 4; and the assembling member 122 is capable of being pulled to move from a side. The third locking member 932 is provided on the assembling member 122, and is a triangular recess 123. Specifically, the assembling member 122 includes a limiting portion 1221 and a rod portion 1222, where two ends of the limiting portion 1221 are respectively connected to the tailstock body 121 and the rod portion 1222. The rod portion 1222 is a free end, and the recess 123 is provided on the limiting portion 1221. When the projection 422 is stuck by the recess 123, the tailstock portion 12 is locked to the protective casing 4; the front end of the built-in slidable sheath 3 is limited by the inner wall of the protective casing 4; and the rear end of the built-in slidable sheath 3 is limited by the tailstock portion 12. When the assembling member 122 is pulled from the side, the projection 422 is unlocked from the recess 123, and the tailstock proportion 12 of the needle holder 1 is unlocked from the protective casing 4 and can be pulled backward.

Figure 8:
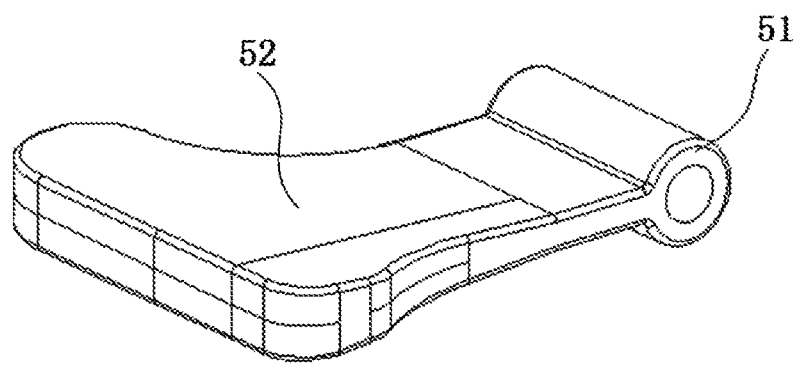
FIG. 8 schematically shows a wing of the manually-retractable intravenous infusion needle assembly according to Example 1 of the invention.

As shown in FIG. 8, the intravenous infusion needle assembly further includes a wing 5, which is sleeved on the assembling member 122. When the wing 5 is pulled from a side, the assembling member 122 is pulled synchronously to move. Specifically, the wing 5 includes a shaft sleeve 51 and a wing blade 52 connected to each other, where the shaft sleeve 51 is rotatably sleeved on the rod portion 1222 of the assembling member 122. The wing 5 is made of an elastic plastic. A surface of the wing blade 52 may be provided with an anti-slip structure such as granular protrusions and patterns to prevent slipping, which avoids the rotation of the needle tip 21 in the blood vessel, reducing the occurrence of damage to the blood vessel and phlebitis in patients who frequently undergo infusion.

As shown in FIGS. 1, 9 and 10, the tubular portion 11, the built-in slidable sheath 3 and the protective casing 4 are compatible with each other in length such that the tubular portion 11 is accommodated in the built-in slidable sheath 3 and the built-in slidable sheath 3 is accommodated in the protective casing 4.

A maximum vertical distance between the needle tube 2 and the outer wall of the lower protective casing 42 is 1.2 mm. It should be specified that the built-in slidable sheath is designed as elongated and through and to have a C-shaped cross section to minimize the vertical distance between the central axis of the needle tube 2 and a bottom of the needle holder 1, which avoids the formation of a large oblique angle between the needle tube 2 and a base of the needle tube 2, preventing the blood vessel from being stabbed by the needle tip 21. In addition, the protective casing 4 can be disassembled into the upper casing 41 and the lower casing 42, which is favorable for the mould-opening production. During the assembling, the built-in slidable sheath 3 is mounted inside the upper casing 41 and the two axial sections 35 of the built-in slidable sheath 3 fit the inner wall of the lower casing 42, enabling the maximum distance between the axis of the needle tube 2 and the outer wall of the protective casing 42 to be no more than 1.5 mm.

The manually-retractable intravenous infusion needle assembly provided herein is assembled as follows.

(1) The needle holder 1 is assembled as follows. The needle tube 2 is mounted at the front end of the needle holder 1. The needle tube 2 may be sleeved with a sleeve 6, and the wing is sleeved on the assembling member 122 of the tailstock portion 12.

(2) The tubular portion 11 of the needle holder 1 is stuck into the built-in slidable sheath 3 to allow the tailstock portion 12 to be located outside the rear end of the built-in slidable sheath 3.

(3) The assembled built-in slidable sheath 3 and needle holder 1 are placed into the upper casing 41.

(4) The lower casing 42 is covered and buckled with the upper casing 41 to form the protective casing 4, and at this time, the third positioning member provided on the lower casing 42 is locked with the third locking member 932 on the assembling member 122 of the tailstock portion 12 and the needle holder 1 is locked to the protective casing 4, and the first locking structure 91 and the second locking structure 92 are both in an unlocked state.

The operation method of this embodiment is specifically described as follows. As shown in FIG. 9, the intravenous infusion needle assembly provided herein is substantially the same with the conventional infusion needle assembly in the operation, and the difference merely exists in that when the needle is pulled out, it is required to press the protective casing 4 by one hand, and the wing 5 on the assembling member 122 is held by the other hand and pulled outward gently such that the third locking member 932 on the assembling member 122 is unlocked from the third positioning member on the lower casing 42; when the wing blade 52 is continuously pulled backward, the needle holder 1 is pulled to the first elastic arm 32 of the first locking member 912 to be locked to the built-in slidable sheath 3, and the built-in slidable sheath 3 is driven to be pulled to the second elastic arm 421 of the second locking member 922 to be locked to the protective casing 4. As shown in FIG. 10, at this time, the needle holder 1 and the built-in slidable sheath 3 both fail to move back and forth, and the needle tube 2 is completely retracted to the protective casing 4 such that the needle tube 2 is pulled out of the patient.

Example 2

Figure 11:
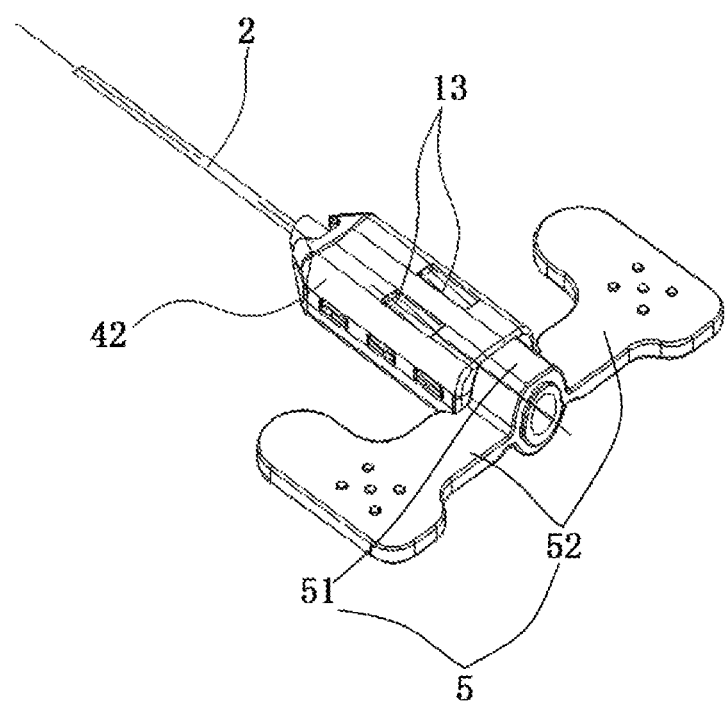
FIG. 11 schematically shows a manually-retractable intravenous infusion needle assembly according to Example 2 of the invention.
Figure 12:
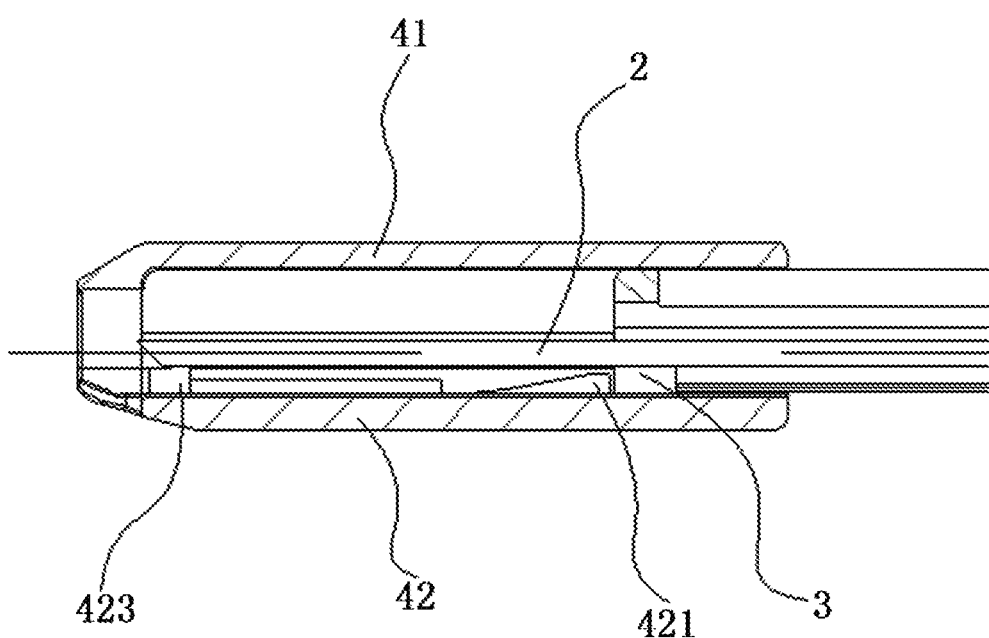
FIG. 12 is a partial longitudinal sectional view of the manually-retractable intravenous infusion needle assembly according to Example 2 of the invention.
Figure 13:
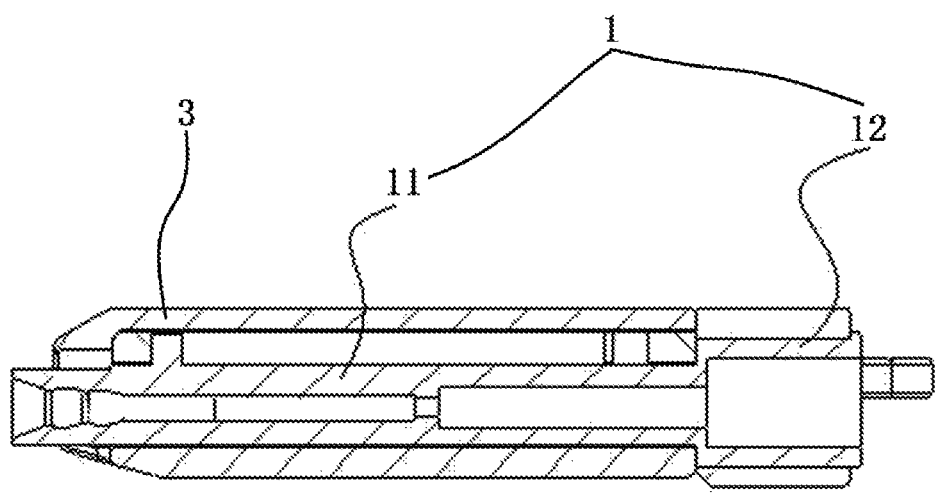
FIG. 13 is a partial sectional view schematically showing the manually-retractable intravenous infusion needle assembly according to Example 2 of the invention.

As shown in FIGS. 11-13, the difference between this embodiment and Example 1 is that the third locking structure 93 adopts a manner in which the needle holder 1 is locked with the front end of the protective casing 4. The third locking structure 93 includes a third positioning member and a third locking member 932. As shown in FIG. 2, the third positioning member is provided at the front end of the outer wall of the tubular portion 11, and includes two side sliding blocks 14 which are symmetrically arranged. It should be noted that the two side sliding blocks 14 of the third positioning member are actually the two side sliding blocks 14 of the first positioning member 911. As shown in FIG. 12, the third locking member 932 is provided at the front end of the inner wall of the lower casing 42, and includes two elastically-deformable bevel bumps 423 which are symmetrically arranged. When the two side sliding blocks 14 are respectively locked by the two bevel bumps 423, the tubular portion 11 is locked in the protective casing 4 and the built-in slidable sheath 3 is simultaneously locked by the tailstock portion 12. When the tubular portion 11 is pulled backward, the two side sliding blocks 14 respectively push the two bevel bumps 423 to generate elastic deformation such that the two side sliding blocks 14 are allowed to slide through the two bevel bumps 423 and the needle holder 1 can be pulled backward to be out of the protective casing 4.

As shown in FIG. 11, the intravenous infusion needle assembly further includes a wing 5, which is sleeved on the tailstock portion 12. The wing 5 can be a single wing or a double wing, and only the double wing is illustrate herein. Two wings of the double wing are symmetrically provided and can be overlapped after folded, which can avoid the rotation of the needle tube 2 in the blood vessel, reducing the occurrence of blood vessel injury and phlebitis in patients who frequently undergo infusion. When the wing is held to be pulled backward, the tailstock portion 12 is pulled synchronously.

In this embodiment, the maximum vertical distance between the needle tube 2 and the outer peripheral surface of the lower casing 42 is 1.3 mm.

The intravenous infusion needle assembly provided herein is assembled as follows.

(1) The needle holder 1 is assembled as follows. The needle tube 2 is mounted at the front end of the needle holder 1. The needle tube 2 may be sleeved with a sleeve 6 and the wing 5 is sleeved on the tailstock portion 12.

(2) The tubular portion 11 of the needle holder 1 is stuck into the built-in slidable sheath 3 to allow the tailstock portion 12 and the wing 5 to be located outside the built-in slidable sheath 3.

(3) The assembled built-in slidable sheath 3 and needle holder 1 are placed into the upper casing 41.

(4) The lower casing 42 is covered and buckled with the upper casing 41 to form the protective casing 4, and at this time, the third locking member 932 provided on the lower casing 42 is locked with the third positioning member on the tubular portion 11 to allow the needle holder 1 to be locked to the protective casing 4, and the first locking structure 91 and the second locking structure 92 are both in an unlocked state.

The operation method of this embodiment is specifically described as follows. As shown in FIG. 11, the intravenous infusion needle assembly provided herein is exactly the same with the conventional infusion needle assembly in the operation. When the needle is pulled out, it is required to press the protective casing 4 by one hand, and the wing 5 is held by the other hand and pulled backward such that the two side sliding blocks 14 on the front end of the outer wall of the tubular portion 11 respectively press the bevels of the two bevel bumps 423 to generate elastic deformation, which causes that the two side sliding blocks 14 are respectively disengaged from the two bevel bumps 423. When the wing 5 is continuously pulled backward, the needle holder 1 is pulled to the first elastic arm 32 of the first locking member 912 to be locked to the built-in slidable sheath 3, and the built-in slidable sheath 3 is driven to be pulled to the second elastic arm 421 of the second locking member 922 to be locked to the protective casing 4. At this time, the needle holder 1 and the built-in slidable sheath 3 both fail to move back and forth, and the needle tube 2 is completely retracted to the protective casing 4 such that the needle tube 2 is pulled out of the patient.

Example 3

Figure 14:
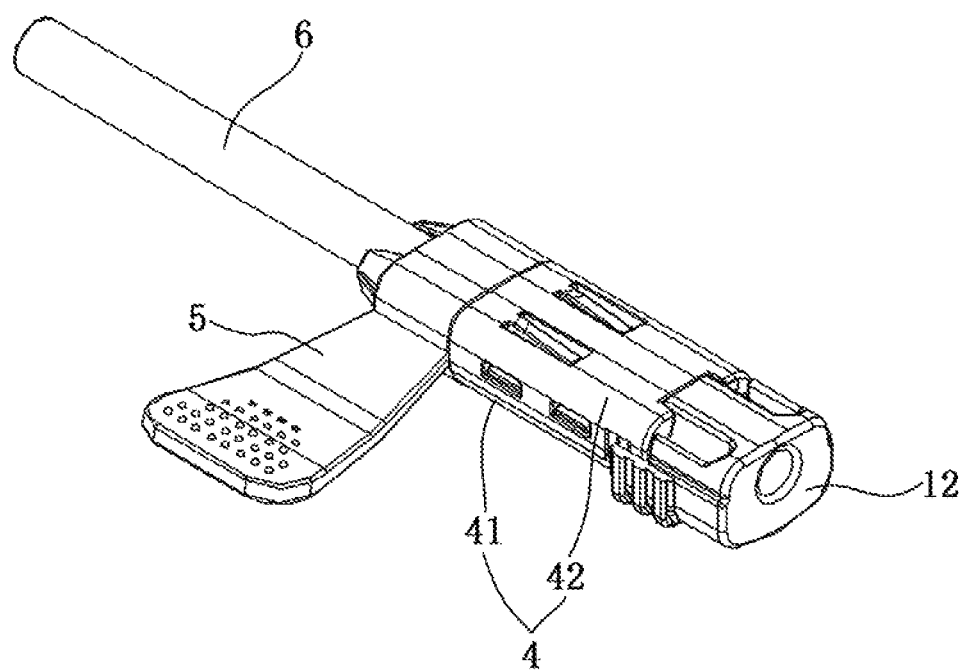
FIG. 14 schematically shows a manually-retractable intravenous infusion needle assembly according to Example 3 of the invention in a closed state before use.
Figure 15:
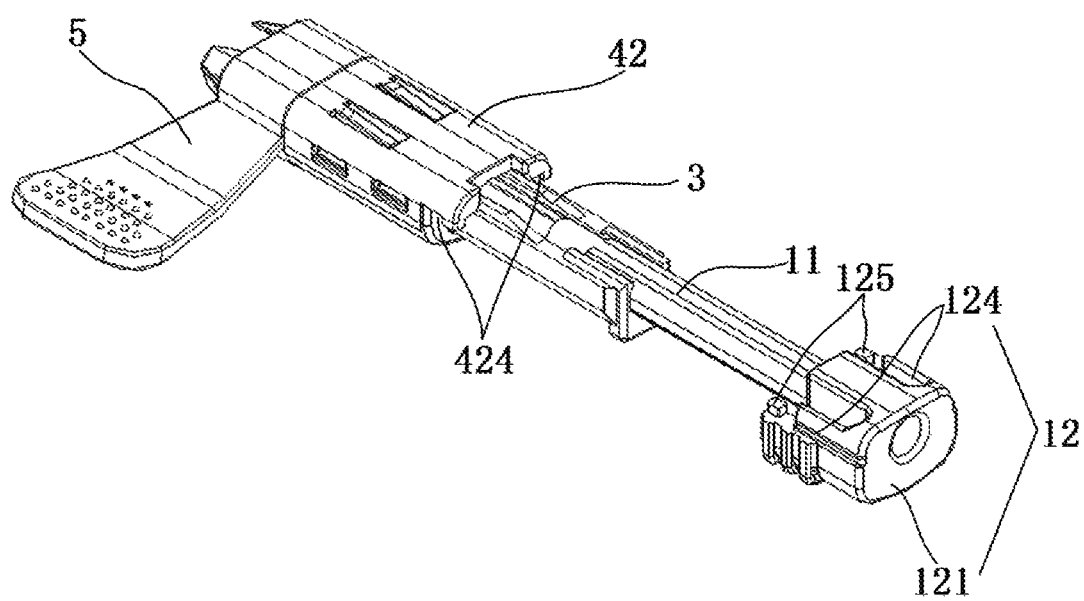
FIG. 15 schematically shows the manually-retractable intravenous infusion needle assembly according to Example 3 of the invention in an open state after use.

As shown in FIGS. 14-15, differing from Embodiments 1-2, the third locking structure 93 in this embodiment adopts a manner in which the needle holder 1 is locked with the rear end of the protective casing 4. The third locking structure 93 includes a third positioning member and a third locking member 932. As shown in FIG. 15, the third positioning member is provided on the tailstock portion 12, where the tailstock portion 12 includes a tailstock body 121 and two pressing members 124. The tailstock body 121 is connected to the tubular portion 11, and the two pressing members 124 are respectively connected to two sides of the tailstock body 121. The two pressing members 124 both are parallel to the central axis of the tubular portion 11, and can be pressed toward each other. The third positioning member includes two hooks 125, which are respectively provided at the front ends of the two pressing members 124. The rear end of the lower casing 42 is provided with the third locking member 932, which includes two slots 424, where the two slots 424 are respectively provided at two sides of the rear end of the protective casing 4. When the two hooks 125 are respectively stuck in the two slots 124, the tailstock portion 12 is locked to the rear end of the protective casing 4; the front end of the built-in slidable sheath 3 is limited by the inner wall of the protective casing 4; and the rear end of the built-in slidable sheath 3 is limited by the tailstock portion 12. When the two pressing members 124 were pressed oppositely, the two hooks 125 are respectively unlocked from the two slots 424 such that the tailstock portion 12 is unlocked from the rear end of the protective casing 4 and can be pulled backward.

The intravenous infusion needle assembly provided herein further includes a wing 5. The wing 5 is a sing wing and is sleeved on the protective casing 4.

The intravenous infusion needle assembly provided herein is assembled as follows.

(1) The needle holder 1 is assembled as follows. The needle tube 2 is mounted at the front end of the needle holder 1 and can be sleeved with a sleeve 6.

(2) The tubular portion 11 of the needle holder 1 is stuck in the built-in slidable sheath 3 to enable that the tailstock portion 12 is located outside the built-in slidable sheath 3.

(3) The assembled built-in slidable sheath 3 and needle holder 1 are placed in the upper casing 41.

(4) The lower casing 42 is covered and bulked with the upper casing 41 to form the protective casing 4. In this case, the third locking member 932 at the rear end of the lower casing 42 is locked with the third positioning member at the tailstock portion 12 to enable the needle holder 1 to be locked to the protective casing 4, and the first locking structure 91 and the second locking structure 92 are both in an unlocked state.

(5) The wing 5 is sleeved on the outer peripheral surface of the protective casing 4.

The operation method is described as follows. As shown in FIG. 14, the infusion needle assembly provided herein is completely the same with the conventional infusion needle assembly in the operation, and an operator can hold the wing 5 to stick the needle. When the needle is pulled out, it is required to press the protective casing 4 by one hand, and press the two pressing members 124 of the tailstock portion 12 at both sides with the other hand such that the third positioning member on the tailstock portion 12 is unlocked from the third locking member 932 at the rear end of the lower casing 42. Then the tailstock portion 12 is pulled backward to allow the needle holder 1 to be pulled to the first elastic arm 32 of the first locking member 912 to be locked to the built-in slidable sheath 3. The built-in slidable sheath 3 is driven to be pulled to the second elastic arm 421 of the second locking member 922 to be locked to the protective casing 4. As shown in FIG. 15, at this time, the needle holder 1 and the built-in slidable sheath 3 both fail to move back and forth, and the needle tube 2 is completely retracted to the protective casing 4 such that the needle tube 2 is pulled out of the patient.

Example 4

Figure 16:
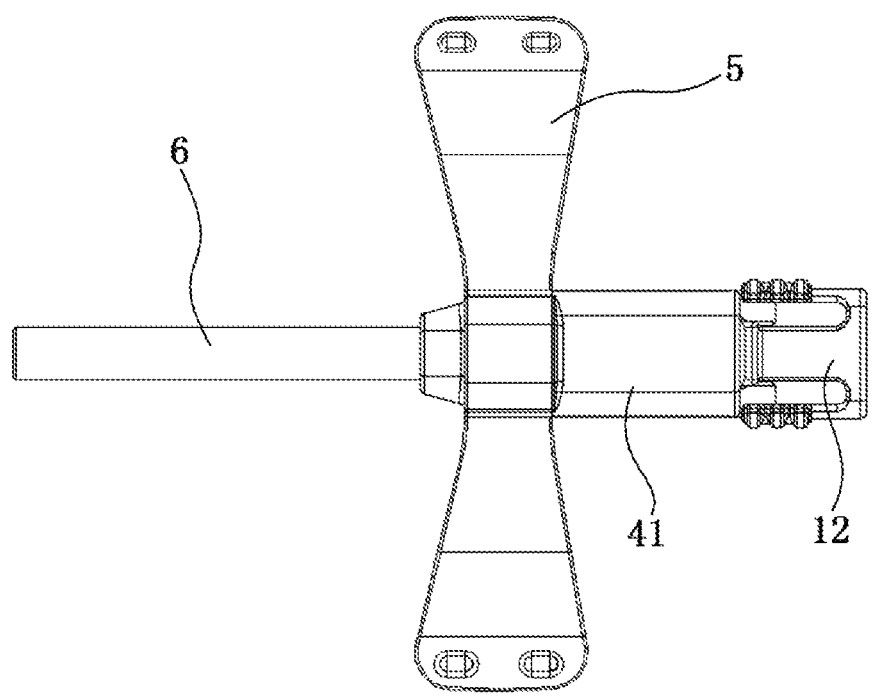
FIG. 16 is a top view of a manually-retractable intravenous infusion needle assembly according to Example 4 of the invention in a closed state before use.
Figure 17:
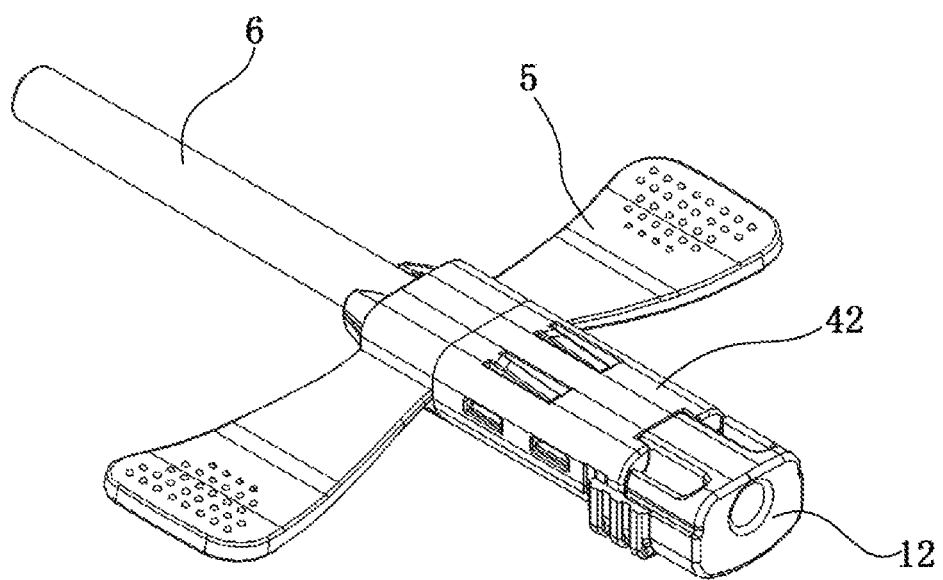
FIG. 17 schematically shows the manually-retractable intravenous infusion needle assembly according to Example 4 of the invention in a closed state before use.
Figure 18:
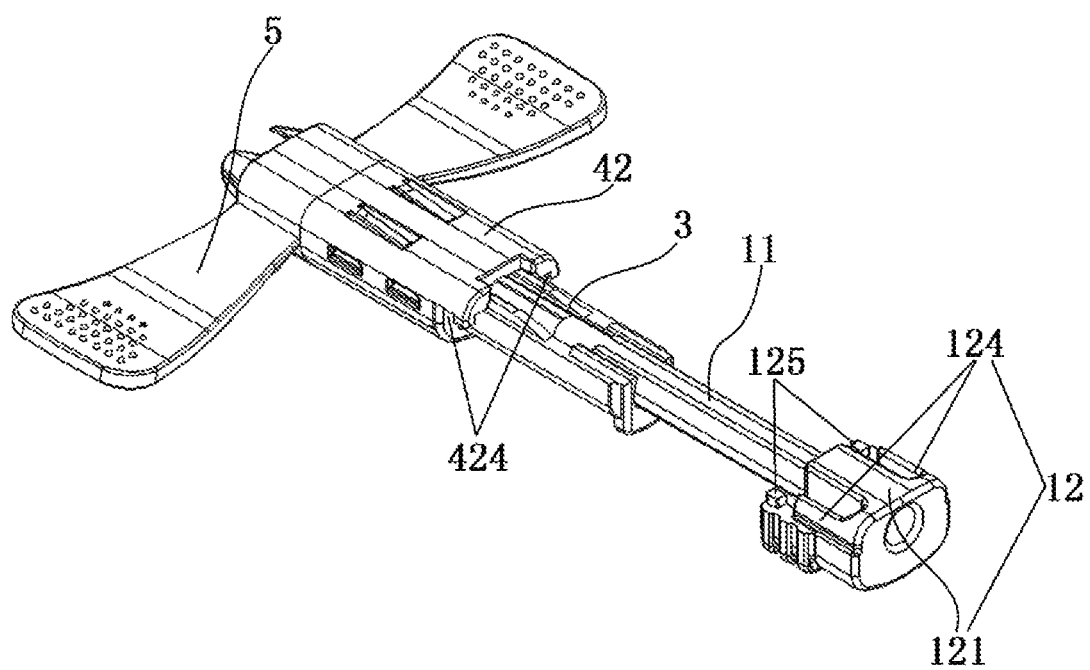
FIG. 18 shows the manually-retractable intravenous infusion needle assembly according to Example 4 of the invention in an open state after use.

As shown in FIGS. 16-18, differing from Example 3, the wing 5 employed herein is a double wing. Two wings of the double wing are symmetrically arranged and can be overlapped after folded in half, which can avoid the rotation of the needle tube 2 in the blood vessel, reducing the occurrence of damage to the blood vessel and phlebitis in patients who frequently undergo infusion. The assembling process and the operation method are consistent with those described in Example 3.

It should be noted that in the above embodiments, the convexity-concavity of the positioning member and the locking member can be interchanged, that is, the positioning member can be a concave portion, and the locking member can be a convex portion, as long as the concave and convex portions can be locked with each other.

Described above are merely preferred embodiments of the invention. It should be understood that various modifications and improvements made by those skilled in the art without departing from the spirit of the invention should fall within the scope of the invention.

What is claimed is:

1. A manually-retractable intravenous infusion needle assembly, comprising:
   a needle holder;
   a needle tube;
   a built-in slidable sheath; and
   a protective casing;
   wherein:
   the needle holder comprises a tubular portion and a tailstock portion; the tubular portion and the tailstock portion are arranged in a front-and-rear manner and are connected to each other; the tubular portion is configured for the arrangement of the needle tube; the tailstock portion is configured to connect a delivery tube;
   the built-in slidable sheath is through and elongated and has a C-shaped cross-section;
   the protective casing is an elongated, through and hollow casing;
   a rear end of the needle tube is mounted inside the tubular portion; the tubular portion is mounted in the built-in slidable sheath and is capable of sliding back and forth; the tailstock portion is provided outside a rear end of the built-in slidable sheath;
   the built-in slidable sheath is mounted in the protective casing and is capable of sliding back and forth; the needle holder is capable of being locked to the protective casing;
   a first locking structure is provided between the needle holder and the built-in slidable sheath to lock the needle holder; a second locking structure is provided between the built-in slidable sheath and the protective casing to lock the built-in slidable sheath; and a third locking structure is provided between the needle holder and the protective casing to lock the needle holder;
   when the third locking structure is unlocked, the needle holder is pulled backward to allow the tubular portion to move to a locking position of the first locking structure such that the tubular portion is locked to the built-in slidable sheath; when the needle holder is continuously pulled backward, the built-in slidable sheath is driven to move to a locking position of the second locking structure to be locked by the protective casing, and in this case, the needle tube is completely covered by the protective casing and a tip of the needle tube does not exceed the protective casing;
   the second locking structure comprises a second positioning member and a second locking member; wherein the second positioning member is provided on the built-in slidable sheath and the second locking member is provided on an inner wall of the protective casing; when the built-in slidable sheath is moved to the locking position of the second locking member, the second positioning member is locked by the second locking member such that the built-in slidable sheath fails to slip off from the protective casing;
   the second positioning member comprises two bumps; the two bumps are respectively provided on two axial sections of the built-in slidable sheath;
   the second locking member comprises two second chutes and two second elastic arms; wherein the two second chutes are axially and symmetrically provided along the protective casing; the two second elastic arms are respectively provided at rear sections of the two second chutes;
   the two bumps are respectively limited to slide within the two second chutes; when the two bumps are moved respectively along the two second chutes to rear ends of the two second chutes, the two second elastic arms are respectively driven by the two bumps to generate elastic deformation to allow the two bumps to pass through; and when the two bumps respectively arrive at the rear ends of the two second chutes, the two second elastic arms recover to a normal state such that the two bumps are locked and fails to slide reversely.

2. The intravenous infusion needle assembly of claim 1, wherein the first locking structure comprises a first positioning member and a first locking member; the first positioning member is provided on an outer wall of the tubular portion and the first locking member is provided on an inner wall of the built-in slidable sheath; when the tubular portion is moved to the locking position of the first locking member, the first positioning member is locked by the first locking member such that the tubular portion fails to slip off from the built-in slidable sheath.

3. The intravenous infusion needle assembly of claim 2, wherein the first positioning member comprises a sliding block; the first locking member comprises a slotted hole and a first elastic arm; the slotted hole is axially provided along the built-in slidable sheath; the first elastic arm is provided at a rear section of the slotted hole; the sliding block is limited to slide within the slotted hole; when the sliding block is moved to a rear end of the slotted hole, the first elastic arm is driven by the sliding block to generate elastic deformation to allow the sliding block to pass through; and when the sliding block arrives at the rear end of the slotted hole, the first elastic arm recovers to a normal state such that the sliding block is locked and fails to slide reversely.

4. The intravenous infusion needle assembly of claim 3, wherein the first positioning member further comprises two side sliding blocks; the two side sliding blocks are respectively provided at two sides of the sliding block;
the first locking member further comprises two first chutes; wherein the two first chutes are axially provided at two sides of the slotted hole along the built-in slidable sheath, respectively; the two side sliding blocks are respectively limited to slide within the two first chutes such that the tubular portion fails to radially slip off from the built-in slidable sheath.

5. The intravenous infusion needle assembly of claim 1, wherein the third locking structure comprises a third locking member and a third positioning member; the third locking member is provided on the tailstock portion and the third positioning member is provided on an outer wall of the protective casing; when the third locking member is locked on the third positioning member, the tailstock portion is locked on the protective casing, a front end of the built-in slidable sheath is limited by the inner wall of the protective casing, and a rear end of the built-in slidable sheath is limited by the tailstock portion; when the third locking member is unlocked from the third positioning member, the needle holder is capable of being pulled backward.

6. The intravenous infusion needle assembly of claim 5, wherein the tailstock portion comprises a tailstock body and an assembling member; the tailstock body is connected to the tubular portion; a side surface of the tailstock body is connected to the assembling member; the assembling member is parallel to a central axis of the tubular portion and clings to the outer wall of the protective casing; the assembling member is capable of being pulled to move from a side surface;
the third locking member is provided on the assembling member; the third locking member comprises a recess and the third positioning member comprises a projection; and when the assembling member is pulled to move from the side surface, the recess is unlocked from the projection.

7. The intravenous infusion needle assembly of claim 6, further comprising a wing; wherein the wing is sleeved on the assembling member; and when the wing is pulled from a side, the assembling member is pulled synchronously.

8. The intravenous infusion needle assembly of claim 1, wherein the third locking structure comprises a third positioning member and a third locking member; the third positioning member is provided on the tubular portion and the third locking member is provided on a front end of the inner wall of the protective casing;
when the third positioning member is locked by the third locking member, the tubular portion is locked inside the protective casing, a front end of the built-in slidable sheath is limited by the inner wall of the protective casing, and a rear end of the built-in slidable sheath is limited by the tailstock portion; when the third positioning member is unlocked from the third locking member, the tubular portion is capable of being pulled out from the built-in slidable sheath.

9. The intravenous infusion needle assembly of claim 8, wherein the third positioning member comprises two side sliding blocks; the two side sliding blocks are symmetrically provided at a front end of an outer wall of the tubular portion;
the third locking member comprises two elastically-deformable bevel bumps; the bevel bumps are symmetrically provided at the front end of the inner wall of the protective casing;
when the two side sliding blocks are respectively locked by the two bevel bumps, the tubular portion is locked inside the protective casing and the built-in slidable sheath is simultaneously limited by the tailstock portion; and when the tubular portion is pulled backward, the two side sliding blocks respectively drive the two bevel bumps to generate elastic deformation such that the two side sliding blocks respectively slide through the two bevel bumps and the needle holder is pulled backward out of the protective casing.

10. The intravenous infusion needle assembly of claim 9, further comprising a wing, wherein the wing is sleeved on the tailstock portion; the wing is a single wing or a double wing; two wings of the double wing are symmetrically provided and are overlapped after folded; and when the wing is held to be pulled backward, the needle holder is synchronously pulled.

11. The intravenous infusion needle assembly of claim 1, wherein the third locking structure comprises a third positioning member and a third locking member; the third positioning member is provided on the tailstock portion and the third locking member is provided at a rear end of the protective casing;
when the third positioning member is locked by the third locking member, the tailstock portion is locked at the rear end of the protective casing, a front end of the built-in slidable sheath is limited by the inner wall of the protective casing and a rear end of the built-in slidable sheath is limited by the tailstock portion; and when the third positioning member is unlocked from the third locking member, the tailstock portion is capable of being pulled backward to move.

12. The intravenous infusion needle assembly of claim 11, wherein the tailstock portion comprises a tailstock body and two pressing members; the tailstock body is connected to the tubular portion; the two pressing members are respectively connected to two sides of the tailstock body; the two pressing members are both parallel to a central axis of the tubular portion; the two pressing members are capable of being oppositely pressed;

the third positioning member comprises two hooks, wherein the two hooks are respectively provided at front ends of the two pressing members;

the third locking member comprises two slots, wherein the two slots are respectively provided at two sides of the rear end of the protective casing; and when the two pressing members are held to be oppositely pressed, the two hooks are respectively unlocked from the two slots.

13. The intravenous infusion needle assembly of claim 12, further comprising a wing; wherein the wing is sleeved on the protective casing; the wing is a single wing or a double wing; two wings of the double wing are symmetrically provided and are overlapped after folded.

14. The intravenous infusion needle assembly of claim 1, wherein the protective casing consists of an upper casing and a lower casing; the upper casing is buckled with the lower casing; the built-in slidable sheath is mounted inside the upper casing; and two axial sections of the built-in slidable sheath fit an inner wall of the lower casing.

15. The intravenous infusion needle assembly of claim 14, wherein a maximum vertical distance between the needle tube and an outer wall of the lower casing is equal to or less than 1.5 mm.

\* \* \* \* \*